US012697077B2

(12) United States Patent
Rane et al.

(10) Patent No.: US 12,697,077 B2
(45) Date of Patent: Aug. 4, 2026

(54) APPARATUS, METHOD, AND COMPUTER-READABLE RECORDING MEDIUM FOR EXECUTING A CUSTOMIZABLE PHYSIOLOGICAL MEASUREMENT SCHEDULE FOR PATIENTS

(71) Applicant: DRÄGERWERK AG & CO. KGAA, Lübeck (DE)

(72) Inventors: Rajesh S. Rane, Andover, MA (US); Lianna Colombo, Phoenix, AZ (US)

(73) Assignee: Drägerwerk AG & Co. KGaA, Lübeck (DE)

( * ) Notice: Subject to any disclaimer, the term of this patent is extended or adjusted under 35 U.S.C. 154(b) by 533 days.

(21) Appl. No.: 17/461,072

(22) Filed: Aug. 30, 2021

(65) Prior Publication Data

US 2022/0183638 A1 Jun. 16, 2022

Related U.S. Application Data

(60) Provisional application No. 63/123,701, filed on Dec. 10, 2020.

(51) Int. Cl.
*A61B 5/00* (2006.01)
*A61B 5/01* (2006.01)
(Continued)

(52) U.S. Cl.
CPC .............. *A61B 5/7475* (2013.01); *A61B 5/01* (2013.01); *A61B 5/021* (2013.01); *A61B 5/024* (2013.01);
(Continued)

(58) Field of Classification Search
None
See application file for complete search history.

(56) References Cited

U.S. PATENT DOCUMENTS 9,486,154 B2 * 11/2016 Fu .............................. A61B 5/33
10,070,805 B1 * 9/2018 Friedman ............... G08B 21/04
(Continued)

OTHER PUBLICATIONS

WelchAllyn.(Jun. 2015).Connex Spot Monitor—Directions for Use https://image.tigermedical.com/Manuals/WEL71XX-B-20150625161642677.pdf (Year: 2015).*
(Continued)

*Primary Examiner* — Benjamin J Klein
*Assistant Examiner* — Willow Grace Welch
(74) *Attorney, Agent, or Firm* — Nolte Lackenbach Siegel

(57) ABSTRACT

An electronic device, method, and computer-readable recording medium execute a customizable physiological measurement schedule for measuring one or more physiological parameters of a patient. A display displays information related to the patient including physiological data, and a memory is configured to store one or more programs. The one or more processors execute the one or more programs to provide a graphical user interface ("GUI") on the display including a customizable measurement schedule. An input is received directed to one or more measurement times and corresponding measurement intervals of the one or more physiological parameters to the customizable measurement schedule using a first selection. When the customizable measurement schedule is executed, the one or more programs when executed by the one or more processors provide a first visible indication as each measurement time and corresponding measurement interval of the customizable measurement schedule is completed.

29 Claims, 11 Drawing Sheets

(51) Int. Cl.
  *A61B 5/021*     (2006.01)
  *A61B 5/024*     (2006.01)
  *A61B 5/145*     (2006.01)

(52) U.S. Cl.
  CPC ...... *A61B 5/14532* (2013.01); *A61B 5/14542*
               (2013.01); *A61B 5/7264* (2013.01)

(56)                    References Cited

U.S. PATENT DOCUMENTS

| | | | |
|---|---|---|---|
| 11,089,980 B1 * | 8/2021 | Biesinger | G16H 40/60 |
| 2004/0034289 A1 * | 2/2004 | Teller | A61B 5/7475 |
| | | | 600/300 |
| 2007/0239070 A1 * | 10/2007 | Hwang | A61B 5/0059 |
| | | | 600/587 |
| 2019/0148010 A1 * | 5/2019 | Aliamiri | A61B 5/0002 |
| | | | 705/2 |
| 2019/0279745 A1 * | 9/2019 | Sayadi | H04Q 9/00 |
| 2022/0257151 A1 * | 8/2022 | Lee | G16H 10/60 |

OTHER PUBLICATIONS

Spokane County EMS Protocols dated Oct. 2022, issued by Spo-
kane County EMS Trauma Care Council, (502 pages).

* cited by examiner

APPARATUS, METHOD, AND COMPUTER-READABLE RECORDING MEDIUM FOR EXECUTING A CUSTOMIZABLE PHYSIOLOGICAL MEASUREMENT SCHEDULE FOR PATIENTS

CROSS-REFERENCE TO RELATED APPLICATIONS

This application claims priority to U.S. Patent Application No. 63/123,701 filed Dec. 10, 2020, the contents of which are incorporated herein by reference.

BACKGROUND

Commonly used workflows in physiological measurements for patients are generally standardized with limited flexibility for users for adjustment. For example, commonly used non-invasive blood pressure (NIBP) measurements include a single measurement, continuous measurements (e.g., 5 minutes total), or venous stasis measurements (e.g., 2 minutes total). However, if a user wants to take multiple physiological measurements with different or varying interval times, there is no efficient and useful way to customize a physiological measurement schedule for a patient.

For example, depending on the condition and location of the patient (e.g., hospital emergency situations), it may be critical to take multiple physiological measurements with different or varying interval times. At present, if multiple physiological measurements with different or varying interval times are needed, the user must manually record timestamps, calculate intervals, and start or stop physiological measurements, which may influence the efficiency in clinical workflows.

BRIEF DESCRIPTION OF THE DRAWINGS

In the drawings, like reference numbers generally indicate identical, functionally similar, and/or structurally similar elements.

DETAILED DESCRIPTION

Figure 1:
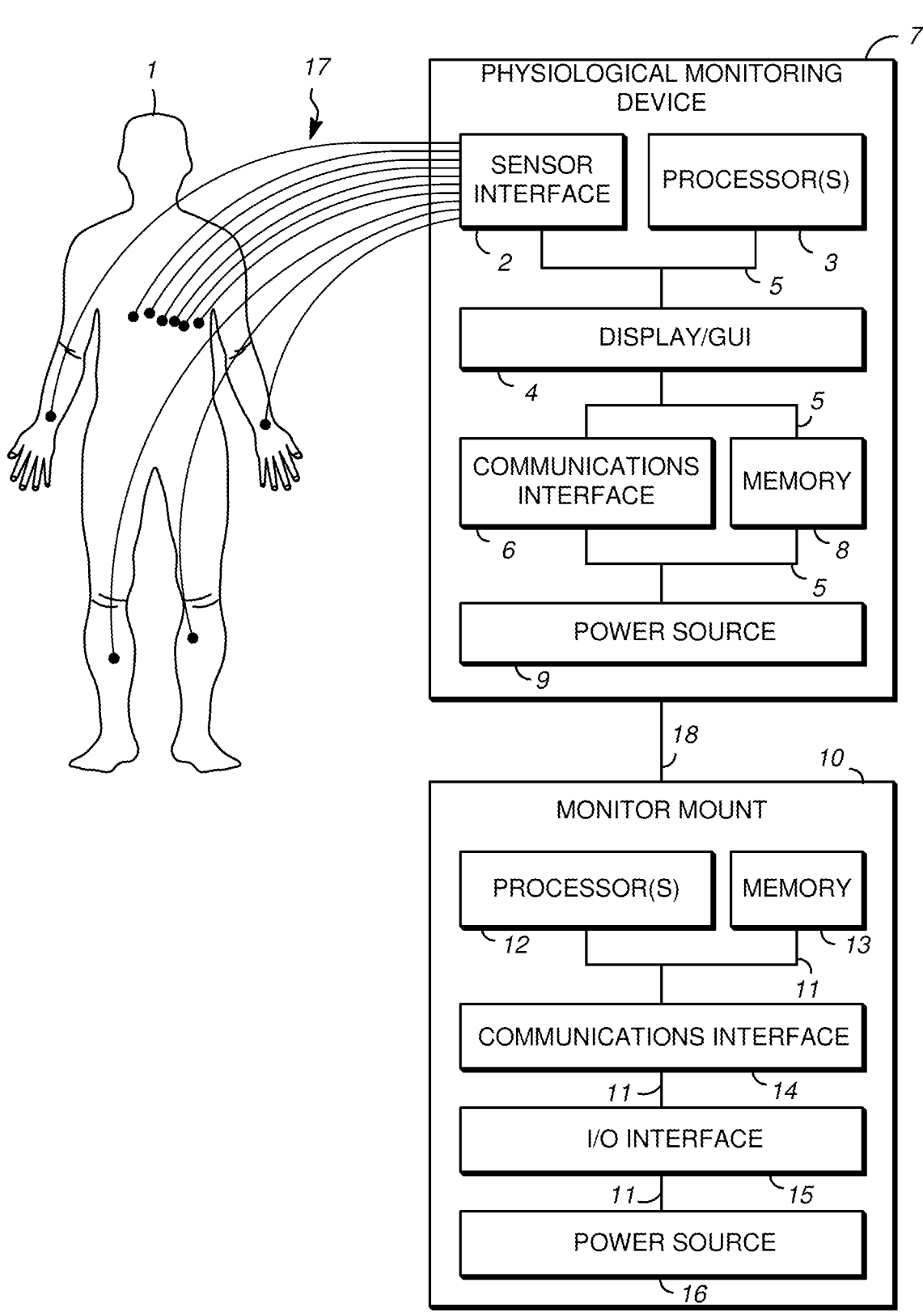
FIG. 1 is a schematic diagram of an example of a system capable of executing a customizable physiological measurement schedule for measuring physiological parameters according to an embodiment of the present disclosure.

The following detailed description is made with reference to the accompanying drawings and is provided to assist in a comprehensive understanding of various example embodiments of the present disclosure. The following description includes various details to assist in that understanding, but these are to be regarded merely as examples and not for the purpose of limiting the present disclosure as defined by the appended claims and their equivalents. The words and phrases used in the following description are merely used to enable a clear and consistent understanding of the present disclosure. In addition, descriptions of well-known structures, functions, and configurations may have been omitted for clarity and conciseness. Those of ordinary skill in the art will recognize that various changes and modifications of the examples described herein can be made without departing from the spirit and scope of the present disclosure.

It would be advantageous and an improvement over the current technology to provide an efficient and useful way to customize a physiological measurement schedule for patients to fulfill different clinical needs and based on patient characteristics (e.g., physiological information, medical condition, patient location, etc.), which reduces stress and cognitive load on clinicians, supports rapid patient assessment and accurate clinical documentation, and improves overall patient care.

The present disclosure provides an apparatus, method, and computer-readable medium that provides a user with more flexibility in configuring or customizing a physiological measurement schedule for patients to fulfill different clinical needs and potentially other considerations.

An embodiment of the present disclosure provides an electronic device capable of executing a customizable physiological measurement schedule for measuring one or more physiological parameters of a patient. The electronic device includes a display configured to display information related to the patient including physiological data, a memory configured to store one or more programs, and one or more processors configured to execute the one or more programs.

The one or more programs when executed by the one or more processors provides a graphical user interface ("GUI") on the display. The GUI includes a customizable measurement schedule for the patient with one or more selections. Moreover, the one or more programs, when executed by the one or more processors. receives an input directed to one or more measurement times and corresponding measurement intervals of the one or more physiological parameters for the patient to the customizable measurement schedule using a first selection among the one or more selections, and executes the customizable measurement schedule.

The one or more programs when executed by the one or more processors provides a first visible indication as each measurement time and corresponding measurement interval of the customizable measurement schedule is completed.

In an embodiment of the present disclosure, the one or more processors are further configured to execute the one or more programs to subtract one or more measurement times and corresponding measurement intervals from the customizable measurement schedule using a second selection among the one or more selections.

In an embodiment of the present disclosure, the customizable measurement schedule is related to discrete or continuous measurements of any one of non-invasive blood pressure ("NIBP"), temperature (e.g., temperature spot-check), heart rate, an electrocardiogram ("ECG"), non-invasive peripheral oxygen saturation (SpO2), end tidal carbon dioxide ($etCO2$), apnea of the patient, neuromuscular transmission ("NMT"), cardiac output ("CO") and glucose concentration. For example, the customizable measurement schedule is related to discrete measurements of at least one of NIBP, NMT or glucose concentration. The one or more processors are configured to automatically execute the customizable measurement schedule. In another example, the customizable measurement schedule is related to discrete measurements of CO. The one or more processors are configured to provide visible indications indicating the customizable measurement schedule, such that clinical providers can provide medical procedures for CO measurement.

In an embodiment of the present disclosure, the one or more processors are further configured to execute the one or more programs to provide a second visible indication indicating the execution of the customizable measurement schedule. Each of one or more measurement times indicates a number of times a measurement is to be taken and the corresponding time interval indicates a time interval for conducting the measurement, and the one or more selections includes one or more selectable measurement schedules.

In an embodiment of the present disclosure, the electronic device further includes a sensor interface configured to receive physiological data from physiological sensors connected to a patient, and a communication interface for receiving location information of the patient. The one or more processors are further configured to execute the one or more programs to provide an indication that adjustments are desired (or needed) to the customizable measurement schedule based on the physiological data and the location information.

An embodiment of the present disclosure provides a method of executing a customizable physiological measurement schedule for measuring one or more physiological parameters of a patient.

The method includes providing a graphical user interface ("GUI") on a display. The GUI includes a customizable measurement schedule for the patient with one or more selections. The method includes receiving an input directed to one or more measurement times and corresponding measurement intervals of the one or more physiological parameters for the patient to the customizable measurement schedule using a first selection among the one or more selections, and executing the customizable measurement schedule.

The method also includes providing a first visible indication as each measurement time and corresponding measurement interval of the customizable measurement schedule is completed.

In an embodiment of the present disclosure, the method further includes subtracting one or more measurement times and corresponding measurement intervals from the customizable measurement schedule using a second selection among the one or more selections.

The customizable measurement schedule can be related to discrete or continuous measurements of any one of non-invasive blood pressure ("NIBP"), temperature (e.g., temperature spot-check), heart rate, an electrocardiogram (ECG), non-invasive peripheral oxygen saturation (SpO2), end tidal carbon dioxide ($etCO2$), apnea of the patient, neuromuscular transmission ("NMT"), and cardiac output ("CO") and glucose concentration.

In an embodiment of the present disclosure, the method further includes providing a second visible indication indicating the execution of the customizable measurement schedule. Each of one or more measurement times indicates a number of times a measurement is to be taken and the corresponding time interval indicates a time interval for conducting the measurement, and the one or more selections includes one or more selectable measurement schedules.

In an embodiment of the present disclosure, the method further includes receiving location information of the patient, receiving physiological data from the patient, and providing an indication that adjustments are recommended to the customizable measurement schedule based on physiological data and the location information.

An embodiment described in the present disclosure provides a non-transitory computer-readable recording medium that stores one or more programs which, when executed by a respective processor, performs the steps of the method(s) described herein.

FIG. 1 is a schematic diagram of a system for displaying transport indicators related to a patient on a physiological monitoring device. As shown in FIG. 1, the system includes a physiological monitoring device 7 capable of receiving physiological data from various sensors 17 connected to a patient 1, and a monitor mount 10 to which the physiological monitoring device 7 is removably mounted or docked.

In general, it is contemplated by the present disclosure that the physiological monitoring device 7 and the monitor mount 10 include electronic components or electronic computing devices operable to receive, transmit, process, store, and/or manage patient data and information associated performing the functions of the system, which encompasses any suitable processing device adapted to perform computing tasks consistent with the execution of computer-readable instructions stored in a memory or a computer-readable recording medium.

Further, any, all, or some of the computing devices in the physiological monitoring device 7 and the monitor mount 10 may be adapted to execute any operating system, including Linux, UNIX, Windows Server, etc., as well as virtual machines adapted to virtualize execution of a particular operating system, including customized and proprietary operating systems. The physiological monitoring device 7 and the monitor mount 10 are further equipped with components to facilitate communication with other computing devices over one or more network connections, which may include connections to local and wide area networks, wireless and wired networks, public and private networks, and any other communication network enabling communication in the system.

As shown in FIG. 1, the physiological monitoring device 7 is, for example, a patient monitor implemented to monitor various physiological parameters of the patient 1 via the sensors 17. The physiological monitoring device 7 includes a sensor interface 2, one or more processors 3, a display/GUI 4, a communications interface 6, a memory 8, and a power source 9. The sensor interface 2 can be implemented in software or hardware and used to connect via wired and/or wireless connections to one or more physiological sensors 17 and/or medical devices for gathering physiological data from the patient 1.

The data signals from the sensors 17 include, for example, data related to an electrocardiogram ("ECG"), non-invasive peripheral oxygen saturation (SpO2), non-invasive blood pressure ("NIBP"), temperature, and/or tidal carbon dioxide ($etCO2$), apnea detection, and other similar physiological data. The one or more processors 3 are used for controlling the general operations of the physiological monitoring device 7. Each one of the one or more processors 3 can be, but are not limited to, a central processing unit ("CPU"), a hardware microprocessor, a multi-core processor, a single core processor, a field programmable gate array ("FPGA"), a microcontroller, an application specific integrated circuit ("ASIC"), a digital signal processor ("DSP"), or other similar processing device capable of executing any type of instructions, algorithms, or software for controlling the operation and performing the functions of the physiological monitoring device 7.

The display/GUI 4 is for displaying various patient data and hospital or patient care information and includes a user interface implemented for allowing communication between a user and the physiological monitoring device 7. The display/GUI 4 may include, but is not limited to, a keyboard, a liquid crystal display (LCD), cathode ray tube (CRT), thin film transistor (TFT), light-emitting diode (LED), high definition (HD) or other similar display device with touch screen capabilities. The patient information displayed can, for example, relate to the measured physiological parameters of the patient 1 (e.g., blood pressure, heart related information, pulse oximetry, respiration information, etc.) as well as information related to the transporting of the patient 1 (e.g., transport indicators). The use of transport indicators will be described in more detail with reference to FIGS. 4-6.

The communications interface 6 allows the physiological monitoring device 7 to directly or indirectly (via, for example, the monitor mount 10) to communicate with one or more computing networks and devices. The communications interface 6 can include various network cards, interfaces or circuitry to enable wired and wireless communications with such computing networks and devices. The communications interface 6 can also be used to implement, for example and without limitation, a BLUETOOTH® connection, a cellular network connection, and/or a WIFI® connection. Other wireless communication connections implemented using the communications interface 6 include wireless connections that operate in accordance with, but are not limited to, IEEE802.11 protocol, a Radio Frequency For Consumer Electronics ("RF4CE") protocol, ZIGBEE® protocol, and/or IEEE802.15.4 protocol.

Additionally, the communications interface 6 can enable direct (i.e., device-to-device) communications (e.g., messaging, signal exchange, etc.) such as from the monitor mount 10 to the physiological monitoring device 7 using, for example, a Universal Serial Bus ("USB") connection. The communications interface 6 can also enable direct device-to-device connection to other devices such as to a tablet, personal computer ("PC"), or similar electronic device, or to an external storage device or memory.

The memory 8 can be a single memory or one or more memories or memory locations that may include, but are not limited to, a random access memory ("RAM"), a memory buffer, a hard drive, a database, an erasable programmable read only memory ("EPROM"), an electrically erasable programmable read only memory ("EEPROM"), a read only memory ("ROM"), a flash memory, hard disk or any other various layers of memory hierarchy. The memory 8 can be used to store any type of instructions and patient data associated with algorithms, processes, or operations for controlling the general functions and operations of the physiological monitoring device 7.

The power source 9 can include a self-contained power source such as a battery pack and/or include an interface to be powered through an electrical outlet (either directly or by way of the monitor mount 10). The power source 9 can also be a rechargeable battery that can be detached allowing for replacement. In the case of a rechargeable battery, a small built-in back-up battery (or super capacitor) can be provided for continuous power to be provided to the physiological monitoring device 7 during battery replacement. Communication between the components of the physiological monitoring device 7 (e.g., 2, 3, 4, 6, 8, and 9) are established using an internal bus 5.

As shown in FIG. 1, the physiological monitoring device 7 is connected to the monitor mount 10 via a connection 18 that establishes a communication connection between, for example, the respective communications interfaces 6, 14 of the devices 7, 10. The connection 18 enables the monitor mount 10 to detachably secure the physiological monitoring device 7 to the monitor mount 10. In this regard, "detachably secure" means that the monitor mount 10 can secure the physiological monitoring device 7, but the physiological monitoring device 7 can be removed or undocked from the monitor mount 10 by a user when desired. The connection 18 may include, but is not limited to, a Universal Serial Bus ("USB") connection, parallel connection, a serial connection, coaxial connection, a High-Definition Multimedia Interface ("HDMI") connection, or other similar connection known in the art connecting to electronic devices.

The monitor mount 10 includes one or more processors 12, a memory 13, a communications interface 14, an I/O interface 15, and a power source 16. The one or more processors 12 are used for controlling the general operations of the monitor mount 10. Each one of the one or more processors 12 can be, but are not limited to, a central processing unit ("CPU"), a hardware microprocessor, a multi-core processor, a single core processor, a field programmable gate array ("FPGA"), a microcontroller, an application specific integrated circuit ("ASIC"), a digital signal processor ("DSP"), or other similar processing device capable of executing any type of instructions, algorithms, or software for controlling the operation and performing the functions of the monitor mount 10.

The memory 13 can be a single memory or one or more memories or memory locations that include, but are not limited to, a random access memory ("RAM"), a memory buffer, a hard drive, a database, an erasable programmable read only memory ("EPROM"), an electrically erasable programmable read only memory ("EEPROM"), a read only memory ("ROM"), a flash memory, hard disk or any other various layers of memory hierarchy. The memory can be used to store any type of instructions associated with algorithms, processes, or operations for controlling the general functions and operations of the monitor mount 10.

The communications interface 14 allows the monitor mount 10 to communicate with one or more computing networks and devices (e.g., the physiological monitoring device 7). The communications interface 14 can include various network cards, interfaces or circuitry to enable wired and wireless communications with such computing networks and devices. The communications interface 14 can also be used to implement, for example, a BLUETOOTH® connection, a cellular network connection, and a WIFI® connection. Other wireless communication connections implemented using the communications interface 14 include wireless connections that operate in accordance with, but are not limited to, IEEE802.11 protocol, a Radio Frequency For Consumer Electronics ("RF4CE") protocol, ZIGBEE® protocol, and/or IEEE802.15.4 protocol.

The communications interface 14 can also enable direct (i.e., device-to-device) communications (e.g., messaging, signal exchange, etc.) such as from the monitor mount 10 to the physiological monitoring device 7 using, for example, a USB connection, coaxial connection, or other similar electrical connection. The communications interface 14 can enable direct (i.e., device-to-device) to other device such as to a tablet, PC, or similar electronic device; or to an external storage device or memory.

The I/O interface 15 can be an interface for enabling the transfer of information between monitor mount 10, one or more physiological monitoring devices 7, and external devices such as peripherals connected to the monitor mount 10 that need special communication links for interfacing with the one or more processors 12. The I/O interface 15 can be implemented to accommodate various connections to the monitor mount 10 that include, but are not limited to, a Universal Serial Bus ("USB") connection, parallel connection, a serial connection, coaxial connection, a High-Definition Multimedia Interface ("HDMI") connection, or other known connection in the art connecting to external devices.

The power source 16 can include a self-contained power source such as a battery pack and/or include an interface to be powered through an electrical outlet (either directly or by way of the physiological monitoring device 7). The power source 16 can also be a rechargeable battery that can be detached allowing for replacement. Communication between the components of the monitor mount 10 (e.g., 12, 13, 14, 15 and 16) are established using an internal bus 11.

Figure 2:
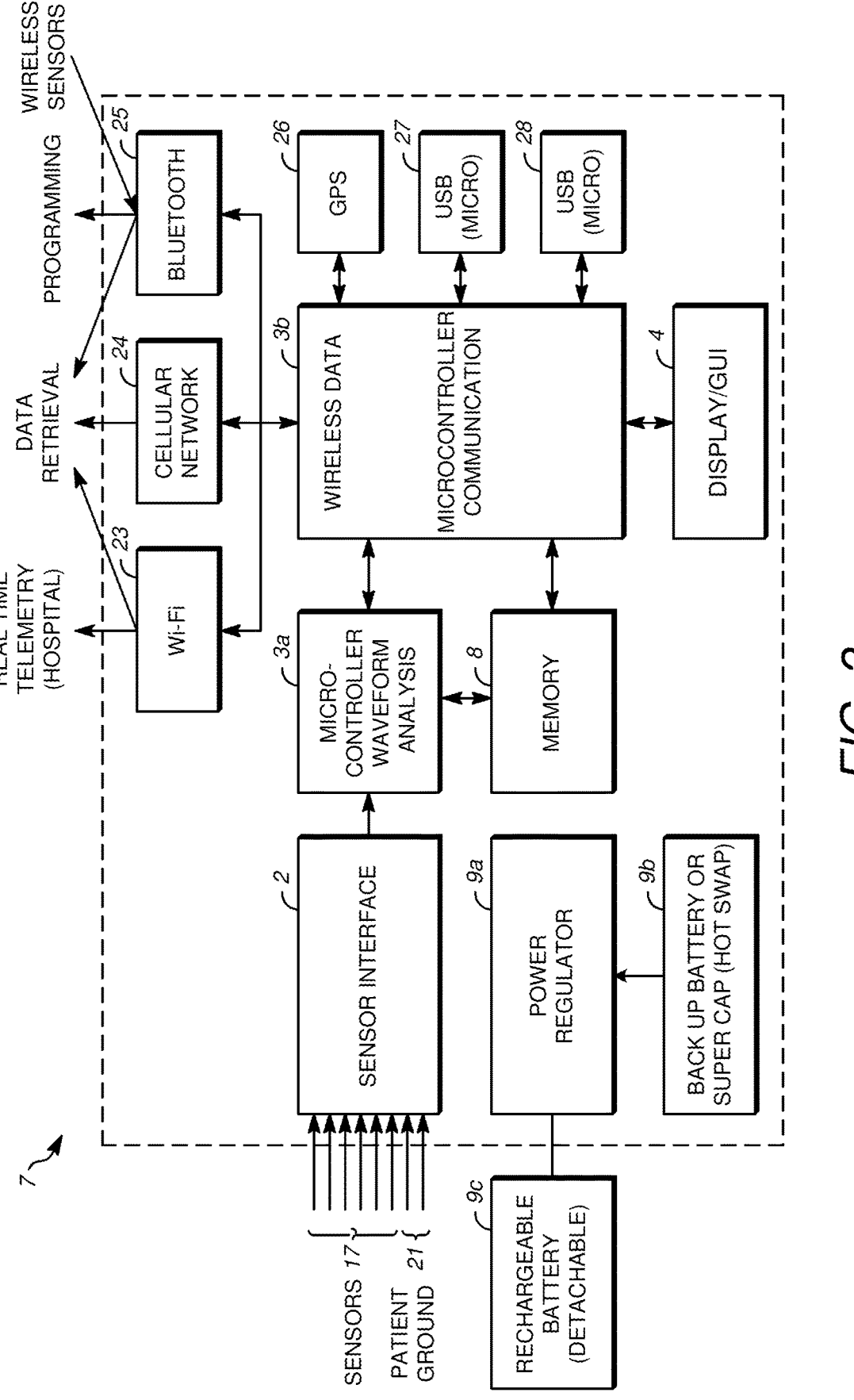
FIG. 2 is a schematic diagram of an example of a physiological monitoring device capable of executing a customizable physiological measurement schedule for measuring physiological parameters according to an embodiment of the present disclosure.

FIG. 2 is a schematic diagram of an example of a physiological monitoring device capable of executing a customizable physiological measurement schedule for measuring physiological parameters according to an embodiment of the present disclosure.

As shown in FIG. 2, the physiological monitoring device 7 is attached to several different types of sensors 17 (including electrodes or other similar devices) known in the art for gathering physiological data related to the patient (e.g., as shown on the left side of FIG. 1). The sensors 17 are communicatively coupled to physiological monitoring device 7 by, for example, a wired connection input to the sensor interface 2. It is contemplated by the disclosure that the physiological monitoring device 7 can also be connected to other wireless sensors using the communications interface 6, which includes circuitry for receiving data from and sending data to one or more devices using, for example, a BLUETOOTH® connection 25. The communications interface 6 shown in FIG. 1 is represented in FIG. 2 by the combination of microcontroller 3b and elements 23-28.

The data signals from the sensors 17 received by the physiological monitoring device 7 include data related to, for example, an ECG, SpO2, NIBP, temperature, and/or etCO2. The data signals received for an ECG sensor and the SpO2 sensor can be analog signals. The data signals for the ECG and the SpO2 are input to the sensor interface 2, which can include an ECG data acquisition circuit and a SpO2 data acquisition circuit. Both the ECG data acquisition circuit and the SpO2 data acquisition circuit include amplifying and filtering circuitry as well as analog-to-digital (A/D) circuitry that convert the analog signal to a digital signal using amplification, filtering, and A/D conversion methods known in the art.

As another example, the data signals related to NIBP, temperature, and etCO2 can be received from sensors 17 to the sensor interface 2, which can include a physiological parameter interface such as serial interface circuitry for receiving and processing the data signals related to NIBP, temperature, and etCO2. The ECG data acquisition circuit, an SpO2 data acquisition circuit, and physiological parameter interface are described as part of the sensor interface 2. However, it is contemplated by the present disclosure that the ECG data acquisition circuit, the SpO2 data acquisition circuit, and physiological parameter interface can be implemented as circuits separate from the sensor interface 2.

The processing performed by the ECG data acquisition circuit, the SpO2 data acquisition circuit, and external physiological parameter interface, none of which are separately shown, produces digital data waveforms that are analyzed by the microcontroller 3a. The processors 3 shown in FIG. 1 are represented in FIG. 2 as microcontrollers 3a and 3b. The microcontroller 3a, for example, analyzes the digital waveforms to identify certain digital waveform characteristics and threshold levels indicative of conditions (e.g., abnormal and normal) of the patient 1 using methods known in the art. The microcontroller 3a includes a memory or uses the memory 8.

The memory 8 stores software or algorithms with executable instructions and the microcontroller 3a can execute a set of instructions of the software or algorithms in association with executing different operations and functions of the physiological monitoring device 7 such as analyzing the digital data waveforms related to the data signals from the sensors 17. The results of the operations performed by the microcontroller 3a are passed to the microcontroller 3b. The microcontroller 3b includes a memory or uses the memory 8.

As noted above, in FIG. 2, the communications interface 6 shown in FIG. 1 is represented by the combination of microcontroller 3b and elements 23-28. For example, the microcontroller 3b includes communication interface circuitry for establishing communication connections with various devices and networks using both wired and wireless connections, and transmitting physiological data, patient and transport information (e.g., transport times and patient location information), results of the analysis by the microcontroller 3a, and alerts and/or alarms to the patient 1, clinicians and/or caregivers. The memory 8 may store software or algorithms with executable instructions and the microcontroller 3b can execute a set of instructions of the software or algorithms in association with establishing the communication connections.

As shown in FIG. 2, wireless communication connections established by the communication interface circuitry of microcontroller 3b include a BLUETOOTH® connection 25, a cellular network connection 24, and a WIFI® connection 23. The wireless communication connections can allow, for example, patient and hospital information, alerts, and physiological data to be transmitted in real-time within a hospital wireless communications network (e.g., WIFI®) as well as allow for patient and hospital information, alerts, and physiological data to be transmitted in real-time to other devices (e.g., via BLUETOOTH® connection 25 and/or cellular network connection 24).

It is also contemplated by the present disclosure that the communication connections established by the microcontroller 3b enable communications over other types of wireless networks using alternate hospital or other medical facility wireless communications such as wireless medical telemetry service ("WMTS"), which can operate at specified frequencies (e.g., 1.4 GHz). Other wireless communication connections can include wireless connections that operate in accordance with, but are not limited to, IEEE802.11 protocol, a Radio Frequency For Consumer Electronics ("RF4CE") protocol, ZIGBEE® protocol, and/or IEEE802.15.4 protocol.

The BLUETOOTH® connection 25 can also be used to provide the transfer of data to a nearby device (e.g., tablet) for review of data and/or changing of operational settings of physiological monitoring device 7. The microcontroller 3b of the physiological monitoring device 7 provides a communication connection by direct wired (e.g., hard-wired) connections for transferring data using, for example, a USB connection 27 to a tablet, PC, or similar electronic device; or using, for example, a USB connection 28 to an external storage device or memory. Additionally, the microcontroller 3b includes a connection to a display 4 including a GUI for displaying patient information, physiological data or measured data, measurement schedules, alerts/alarms for the patient, clinicians and/or caregiver's information. Although the physiological monitoring device 7 is described in FIG. 1 as having two microcontrollers 3a and 3b, it is contemplated by the disclosure of the present application that one microcontroller can be implemented to perform the functions of the two microcontrollers 3a and 3b.

The display 4 includes, for example, a liquid crystal display ("LCD"), thin film transistor ("TFT"), light-emitting diode ("LED"), high definition ("HD") or other similar GUI with touch screen capabilities. The display 4 also includes a GUI that provides a means for inputting instructions or information directly to the physiological monitoring device 7. As shown in FIG. 2, the physiological monitoring device 7 includes a Global Positioning System ("GPS") or other location data system 26 that can be connected to the communication interface circuitry of microcontroller 3b so that the physiological monitoring device can transmit to the clinician, caregiver, or other devices the location of the patient 1 at all times including the location of the patient 1. Additionally, the location of the patient 1 can be used by the microcontroller 3b to determine an estimated time of arrival of the patient 1.

For example, location data provided by the location data system 26, which may include information on a floor level, can be compared to stored information related to a hospital layout or a hospital map as well as information related to a patient's scheduled care (e.g., treatment or procedure scheduled for the patient 1 in a patient care area within the hospital). Based on the comparison results, the microcontroller 3b can determine the estimated time of arrival of the patient 1 to the patient care area within the hospital. The estimated time of arrival can be transmitted by the communication interface circuitry of microcontroller 3b to, for example, the hospital wireless communications system.

Additionally, if it is determined by the microcontroller 3b that the patient 1 is not within the vicinity of the hospital wireless communications system (e.g., based on input from the location data system 26), the pertinent physiological data can be recorded and stored in the memory 8. Additionally, if the BLUETOOTH® connection 25 or WIFI® connection 23 are not available (e.g., out of transmission range or not operable), then the microcontroller 3b can store the physiological data in the memory 8 for later transmission when the BLUETOOTH® connection or WIFI® connection become available.

The power source 9 shown in FIG. 1 is represented by elements 9a-9c in FIG. 2. As shown in FIG. 2, the power can be supplied using a rechargeable battery 9c that can be detached allowing for replacement. The rechargeable battery 9c is, for example, a rechargeable lithium-ion battery. Additionally, a small built-in back-up battery 9b (or super capacitor) is provided for continuous power to the physiological monitoring device 7 during battery replacement. A power regulator or regulation circuit 9a is provided between the rechargeable battery 9c and small back-up battery 9b to control which battery provides power to the physiological monitoring device 7. The physiological monitoring device 7 also includes a patient ground connection 21. The patient ground connection 21 can be used as a ground for single ended unipolar input amplifiers (e.g., precordial leads), or as a ground for bipolar input amplifiers (e.g., limb leads). It is also contemplated by the present disclosure that the power regulator 9a can include a self-contained power source, such as a battery pack, and/or include an interface to be powered through an electrical outlet (either directly or by way of the monitor mount 10). Communication between the components of the physiological monitoring device 7 can be established using an internal bus similar to the internal bus 5 discussed with reference to FIG. 1.

Figure 3:
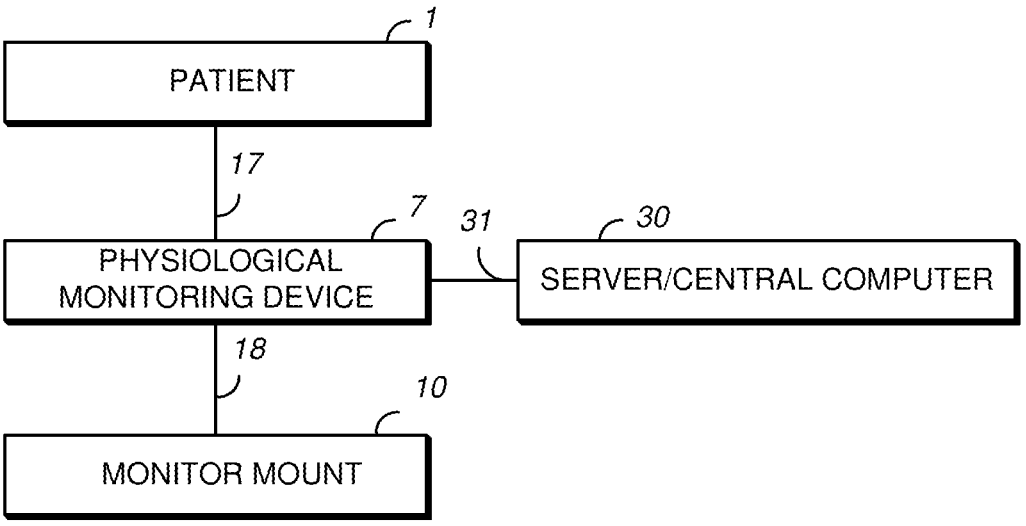
FIG. 3 is a schematic diagram of an example of a system including a server/central computer according to an embodiment of the present disclosure.

FIG. 3 is a schematic diagram of an example of a system including a server/central computer according to an embodiment of the present disclosure. FIG. 3 includes the patient 1, the physiological monitoring device 7, and the monitor mount 10 already discussed with reference to FIGS. 1 and 2. However, FIG. 3 also includes the addition of a server or central computer 30. As shown in FIG. 3, the physiological monitoring device 7 receives physiological data from various sensors 17 connected to the patient 1, and the physiological monitoring device 7 is removably mounted or docked to the monitor mount 10. The physiological monitoring device 7 is connected to the monitor mount 10 via the connection 18 that establishes a communication connection between, for example, the respective communications interfaces 6, 14 of the devices 7, 10. The connection 18 enables the monitor mount 10 to detachably secure the physiological monitoring device 7 to the monitor mount 10.

The connection 18 may include, but is not limited to, a Universal Serial Bus ("USB") connection, parallel connection, a serial connection, coaxial connection, a High-Definition Multimedia Interface ("HDMI") connection, or other similar connection known in the art connecting to electronic devices. The physiological monitoring device 7 can also be connected to a server/central computer 30 via a wired or wireless connection 31 using the communication interface circuitry of the communications interface 6 of the physiological monitoring device 7 described with reference to FIGS. 1 and 2. The server/central computer 30 can be located in or outside care area. For example, the server/central computer 30 can be located at a nurse station or other similar location within the hospital or other medical care facility.

In one embodiment, the physiological monitoring device 7 may transmit, via the connection 31, physiological data collected by the sensors 17 (shown in FIG. 1) and/or other patient information (e.g., measurement schedules, patient location information, alert/alarm information) to the server/central computer 30 for storage and data processing. For example, upon the NIBP measurements with variable intervals configured by users on the physiological monitoring device 7, the NIBP data processed by the physiological monitoring device 7 along with related information may be transmitted and stored in the server/central computer 30.

In another embodiment, the server/central computer 30 may transmit control signals, via the connection 31, to control the functions of the monitoring device 7 and the sensors that are connected to the device. As such, users are allowed to control the physiological measurements performed by the sensors or configure the measurement settings, via the user interface of the server/central computer 30. For example, the server/central computer 30 may allow users to configure NIBP measurements (e.g., customize measurement intervals and/or frequencies) via the user interface of the server/central computer 30 without being in front of the physiological monitoring device 7.

Optionally or additionally, the server/central computer 30 may store the patient's physiological measurements and algorithms to provide recommended measurement configurations to users based on one or more of the patient's physiological parameters, medical history, and care area where the patient is currently located. For example, based on the patient's NIBP trends in a pre-determined time, the patient's medical history and/or the care area where the patient is located, the algorithms in the server/central computer 30 may provide recommended measurement configurations in adjusting NIBP measurement intervals and/or frequencies.

Figure 4:
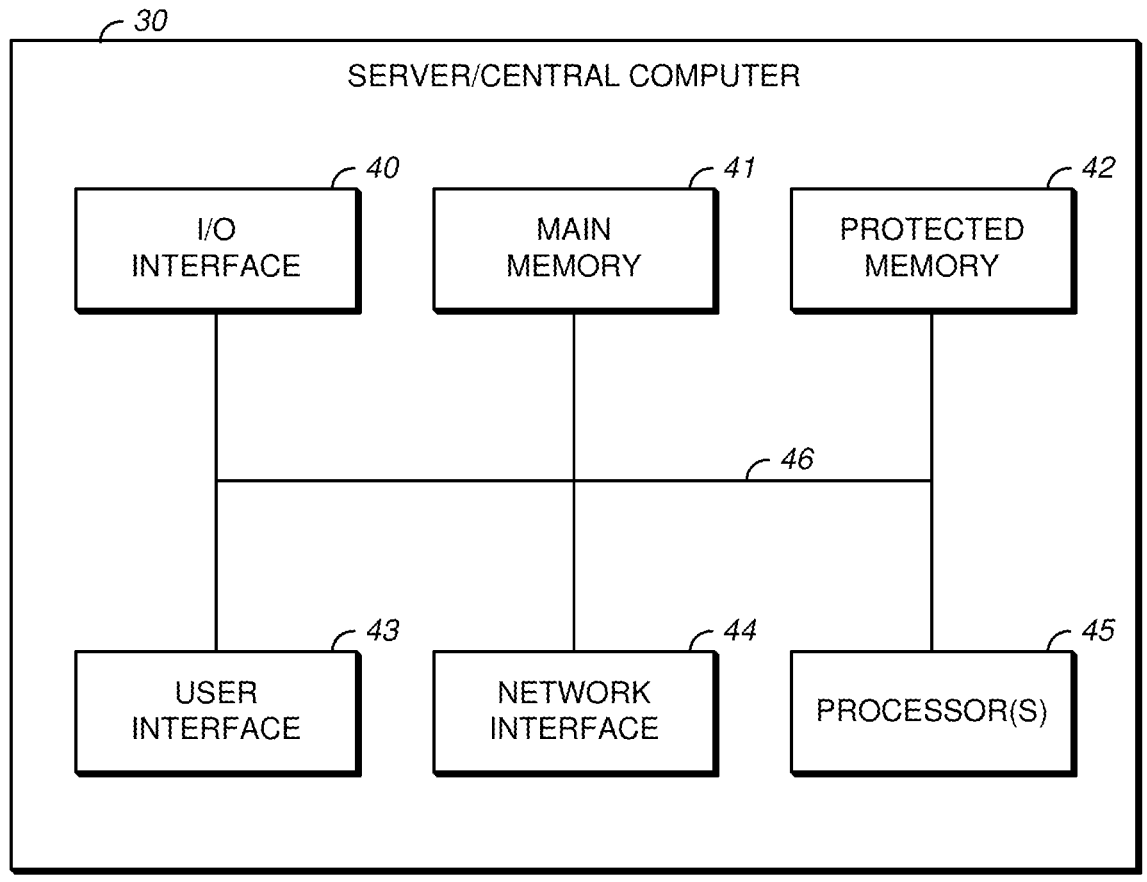
FIG. 4 is schematic diagram of an example of a server/central computer according to an embodiment of the present disclosure.

FIG. 4 is a schematic diagram of an example of a server/central computer according to an embodiment of the present disclosure. As shown in FIG. 4, the exemplary server/central computer 30 includes an I/O interface 40, a main memory 41, a protected memory 42, a user interface 43, a network interface 44, and one or more processors 45.

The I/O interface 40 can be implemented to accommodate various connections to the server/central computer 30 that include, but are not limited to, a Universal Serial Bus ("USB") connection, parallel connection, a serial connection, coaxial connection, a High-Definition Multimedia Interface ("HDMI") connection, or other known connection in the art connecting to external devices. The I/O interface 40 can be an interface for enabling the transfer of information between server/central computer 30, one or more physiological monitoring devices 7, and external devices such as peripherals connected to the server/central computer 30 that need special communication links for interfacing with the one or more processors 45.

The main memory 41 can be used to store any type of instructions associated with algorithms, processes, or operations for controlling the general functions of the server/central computer 30 as well as any operating system such as LINUX®, UNIX®, WINDOWS® Server, or other customized and proprietary operating systems.

The protected memory 42 is, for example, a processor reserved memory of dynamic random access memory ("DRAM") or other reserved memory module or secure memory location for storing more critical information such as confidential or proprietary patient information.

The user interface 43 is implemented for allowing communication between a user and the server/central computer 30. The user interface 43 includes, but is not limited to, a mouse, a keyboard, a liquid crystal display ("LCD"), thin film transistor ("TFT"), light-emitting diode ("LED"), high definition ("HD") or other similar display device with touch screen capabilities. The network interface 44 is a software and/or hardware interface implemented to establish a connection between the server/central computer 30 and one or more physiological monitoring devices or other servers/central computer inside and outside the patient care or hospital environment.

It is contemplated by the present disclosure that that network interface 44 includes software and/or hardware interface circuitry for establishing communication connections with the rest of the system using both wired and wireless connections for establishing connections to, for example, a local area networks ("LANs"), wide area networks ("WANs"), metropolitan area networks ("MANs") personal area networks ("PANs"), and wireless local area networks ("WLANs"), system area networks ("SANs"), and other similar networks.

The one or more processors 45 are used for controlling the general operations of the server/central computer 30. Communication between the components of the server/central computer 30 (e.g., 40-44) are established using an internal bus 46.

FIGS. 5-10 illustrate examples of graphical user interfaces ("GUIs") for executing a customizable physiological measurement schedule for measuring physiological parameters according to embodiments of the present disclosure.

It is contemplated by the present disclosure that the GUIs as shown in FIGS. 5-10 can be generated on the display 4 for allowing interaction with one or more users, by one or more processors 3 executing one or more programs stored in the memory 8 of an electronic device such as, but not limited to, a physiological monitoring device 7, as described with reference to FIGS. 1 and 2. Although the examples in FIGS. 5-10 refer to a physiological monitoring device 7, it is also contemplated by the present disclosure that the GUIs can be implemented on other electronic devices including, but not limited to, a hand-held computing device, a personal computer, an electronic tablet, a smart phone, or other similar hand-held consumer electronic device capable of executing and displaying the GUI. For example, the GUIs as shown in FIGS. 5-10 can be implemented on the user interface 43 (e.g., display) of the server/central computer 30, such that users are allowed to control the functions of the physiological monitoring device 7 and the connected sensors.

Figure 5:
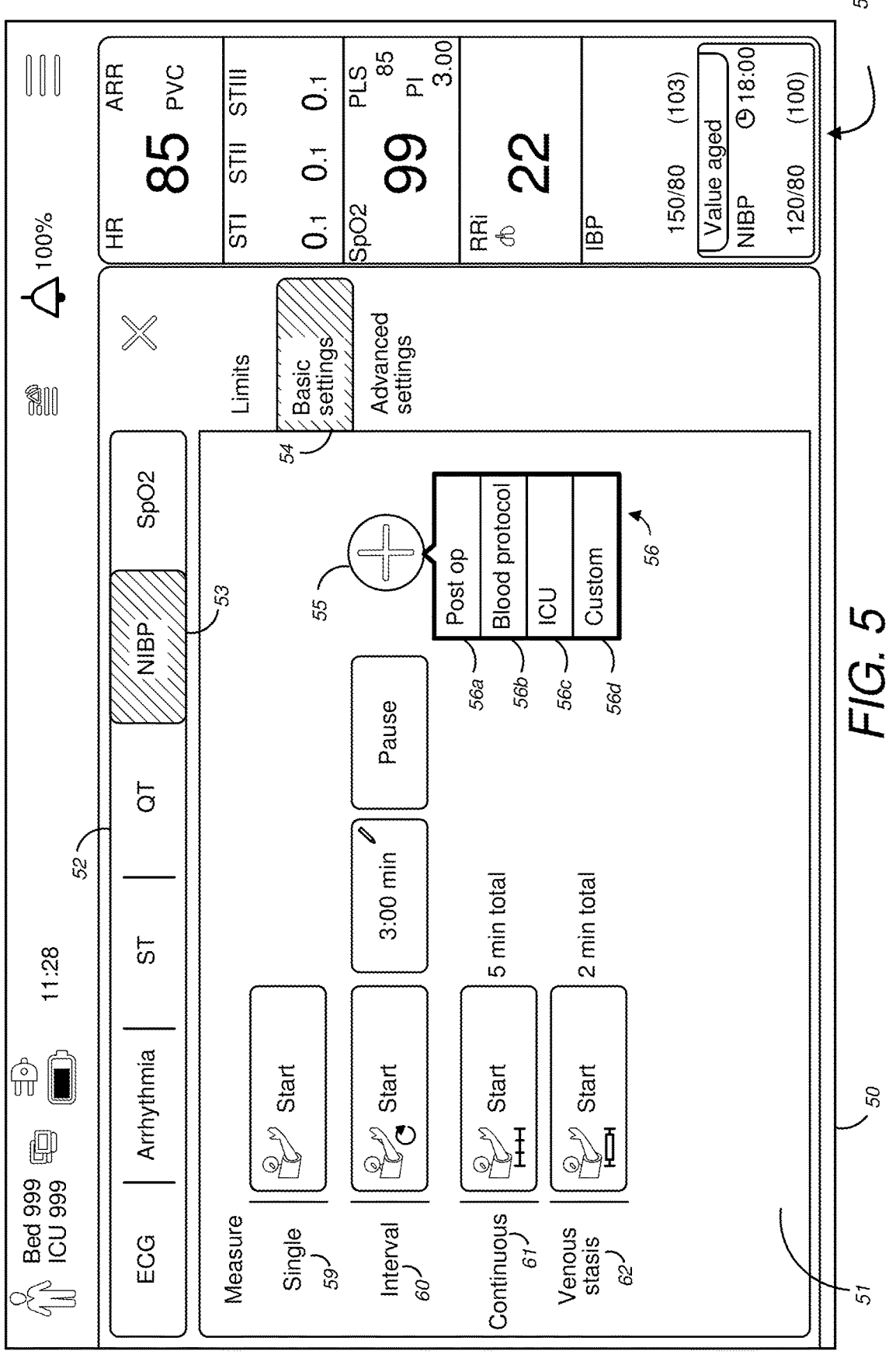
FIGS. 5-10 illustrate examples of graphical user interfaces (GUIs) for executing a customizable physiological measurement schedule for measuring physiological parameters according to embodiments of the present disclosure.

As shown in FIG. 5, the GUI 50 provides selectable measurement schedules 52 for measuring various physiological parameters (e.g., ECG, Arrhythmia, ST segment, QT interval, NIBP, and SpO2) as well as measured patient data 58. The selectable measurement schedules 52 for measuring various physiological parameters (e.g., ECG, Arrhythmia, ST segment, QT interval, NIBP, and SpO2) shown in FIG. 5 are provided merely as an example, and it is contemplated by the present disclosure that the selectable measurements schedules 52 can include schedules for measuring any physiological parameters of the patient measured either discretely or continuously. In FIG. 5, the measured patient data 58 is provided from, for example, the sensors 17 (e.g., monitoring various physiological parameters of the patent 1) to the physiological monitoring device 7 via the sensor interface 2 shown in FIG. 1. FIG. 5 provides an example of a measurement schedule 51 for measuring NIBP of the patient 1. That is, from the GUI 50, a user selects the measurement schedule for NIBP 53 from the selectable measurement schedules 52.

Once the measurement schedule for NIBP 53 is selected, the GUI 50 provides basic settings 54 as well as advanced settings for NIBP measurements provided within the selected measurement schedule. As shown in FIG. 5, the basic settings 54 are selected and the measurement schedule 51 for NIBP provides physiological measurements modes such as single measurement 59, interval 60 measurement or mode (e.g., every 3 minutes a new measurement is taken and recorded), continuous measurement 61 (e.g., the patient's blood pressure is measured continuously for 5 minutes total), and venous stasis measurement 62 (e.g., 2 minutes total). The GUI 50 provides a user with predefined configuration settings in scheduling interval 60 mode for NIBP measurements (e.g., measurement interval of every 3 minutes). While the illustrated example shows intervals of 3 minutes, the intervals could be shorter or longer (e.g., a short as 1 minute, or as long as several hours between measurements). Similarly, the continuous measurement time could be shorter or longer.

To further improve the clinical workflow and reduce the time that clinical providers spend in configuring NIBP settings, the GUI 50 also provides other pre-defined schedules for the interval 60 mode of the measurement schedule 51 for NIBP by using the selection 55 (e.g., "+").

For example, a user selects the selection 55 (e.g., "+") from the measurement schedule 51 for NIBP, and the GUI 50 provides various additional options for pre-defined schedules for the interval mode 60. The additional options can be provided as, for example, a drop-down menu 56 or list of selectable options. As shown in FIG. 5, the pre-defined schedules include post operation 56*a*, blood protocol 56*b*, ICU 56*c* and custom 56*d*, which can be based on different clinical needs. The pre-defined schedules (e.g., 56*a*-56*d*) shown in FIG. 5 are merely examples and it is contemplated by the present disclosure that the pre-defined schedules can include schedules for measuring any physiological parameters of the patient measured either discretely or continuously. The user can select a schedule as desired from the menu without manually creating a custom schedule, or combine the custom schedule with a pre-defined schedule. Stated another way, custom schedules may include both pre-defined and manually created entries.

Figure 6:
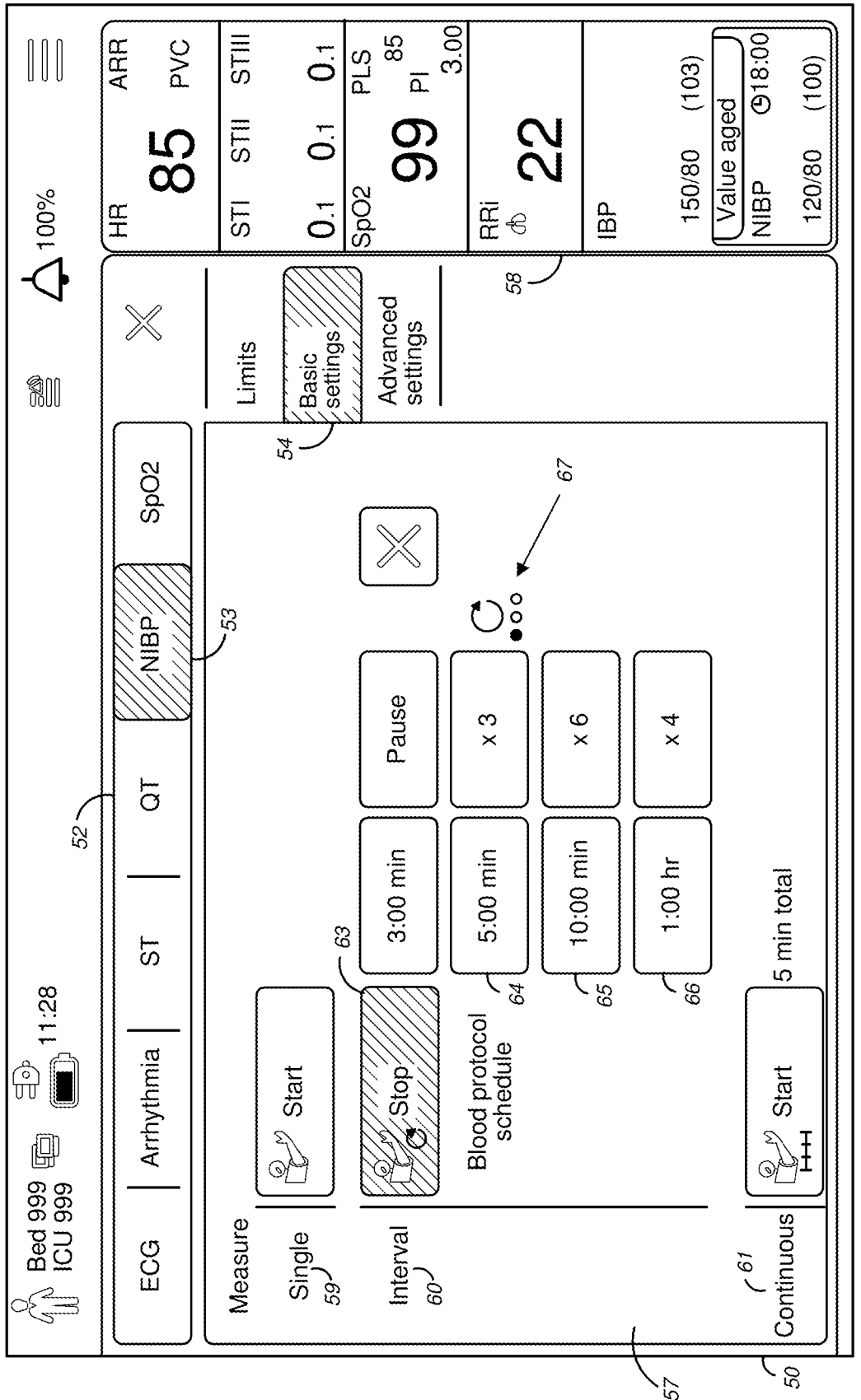

As shown in FIG. 6, the user has selected a blood protocol 56*b* from the drop-down menu or list 56 and the GUI 50 presents a blood protocol schedule 57. The blood protocol schedule 57 can include, for example, repeated NIBP measurements 64 to be taken 3 times (e.g., ×3) with a 5-minute interval between each measurement, followed by NIBP measurements 65 to be taken 6 times (e.g., ×6) with a 10-minute interval and subsequently, NIBP measurements 66 to be taken 4 times (e.g., ×4) with a 1-hour interval. From the blood protocol schedule 57, the user can select "start" (e.g., shown as "stop" 63 once selected) to execute the blood protocol schedule 57, and the execution of the blood protocol schedule 57 can be indicated by a visual indication 67 provided to the user within the blood protocol schedule 57.

As shown in FIG. 6, once "start" 63 is selected the selection changes to "stop" 63. That is, the same selection 63 from the GUI 50 can be used for both starting and stopping the blood protocol schedule 57. Additionally, the visual indication 67 can also be located next to a specific measure schedule (e.g., measure schedule 64) in order to indicate which measurement within a certain cycle is currently in progress. A user can stop the execution of the blood protocol schedule 57 any time by selecting "stop" 63 from the blood protocol schedule 57.

Figure 7:
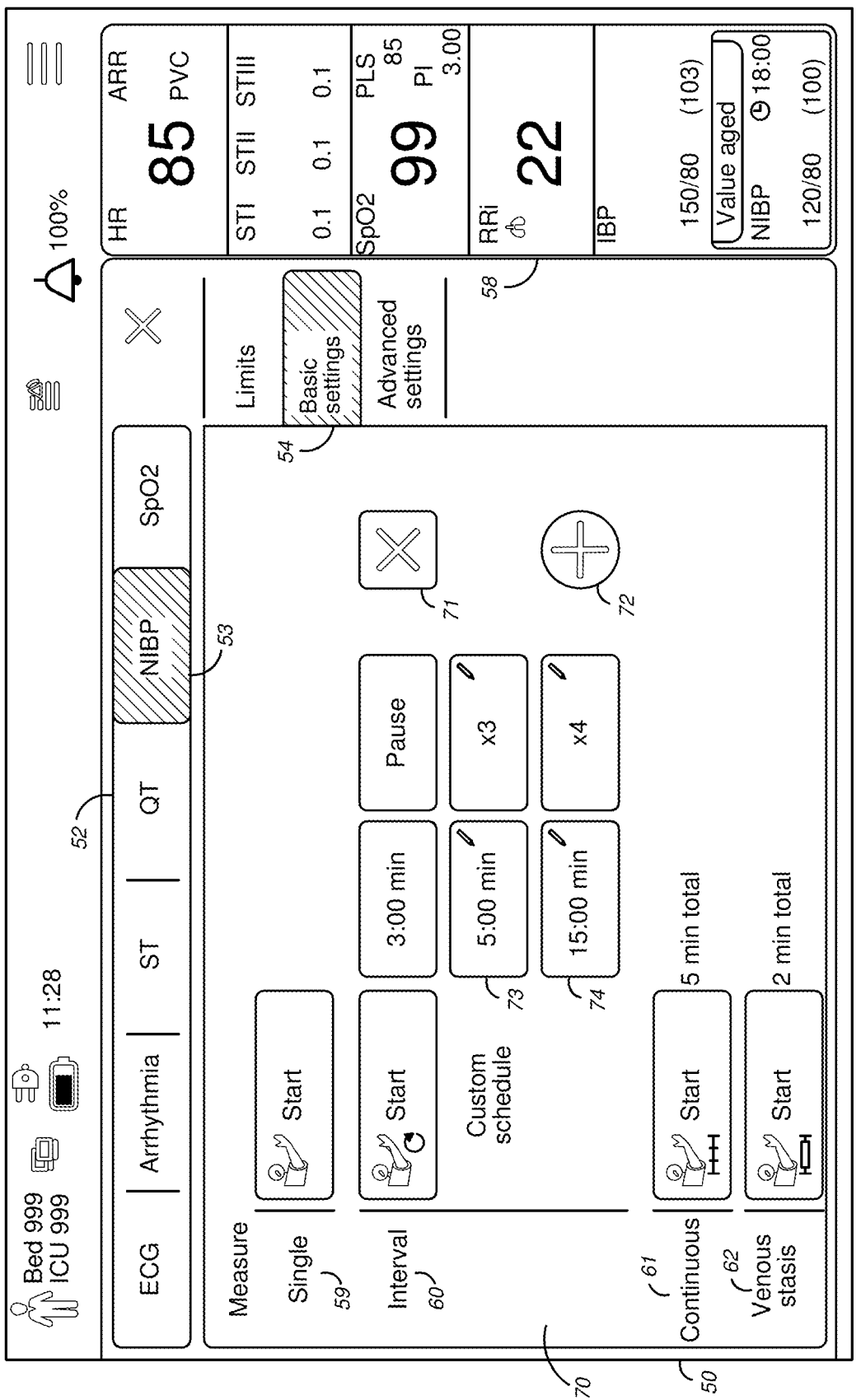

If a user wants to take multiple physiological measurements with different or varying interval times, the user can select "custom" 56*d* from the drop-down menu or list 56 (as illustrated in FIG. 5) and the GUI 50 will present options for creating a custom schedule, as shown in FIG. 7. As shown in FIG. 7, the user has selected a custom 56*d* from the drop-down menu or list 56 and the GUI 50 presents a custom schedule 70. While in the custom schedule 70, the selections 72 (e.g., "+") and 71 (e.g., "×") can be used to add or remove, respectively, one or more measurement schedules to and from the custom schedule 70. For example, from the custom schedule 70, the user can add one or more measurements schedules by using the selection 72 (e.g., "+") and the user can remove one or more measurement schedules by using the selection 71 (e.g., "×").

Although FIG. 7 illustrates one selection 72 (e.g., "+") for adding one or more measurement schedules and one selection 71 (e.g., "×") for removing one or more measurement schedules, it is contemplated by the present disclosure that any number of selections can be included in the GUI 50 for adding or removing measurement schedules as well as adding or removing specific features of the measurement schedules.

As shown in FIG. 7, while in the custom schedule 70, the user has used selection 72 (e.g., "+") to add two measurement schedules to the custom schedule 70. The custom schedule 70 includes one or more cycles of repeated NIBP measurements 73 to be taken three times (e.g., ×3) with a 5-minute interval between each measurement, followed by NIBP measurements to be taken four times (e.g., ×3) with a 15-minute interval between each measurement. The custom schedule 70 allows the user to adjust the numbers of the measurements and intervals. It is also contemplated by the present disclosure that the user is able to select one or more measurement schedules previously used and stored in, for example, the memory 8, 13, 41, 42 of an electronic device 7, 10, 30.

Figure 8:
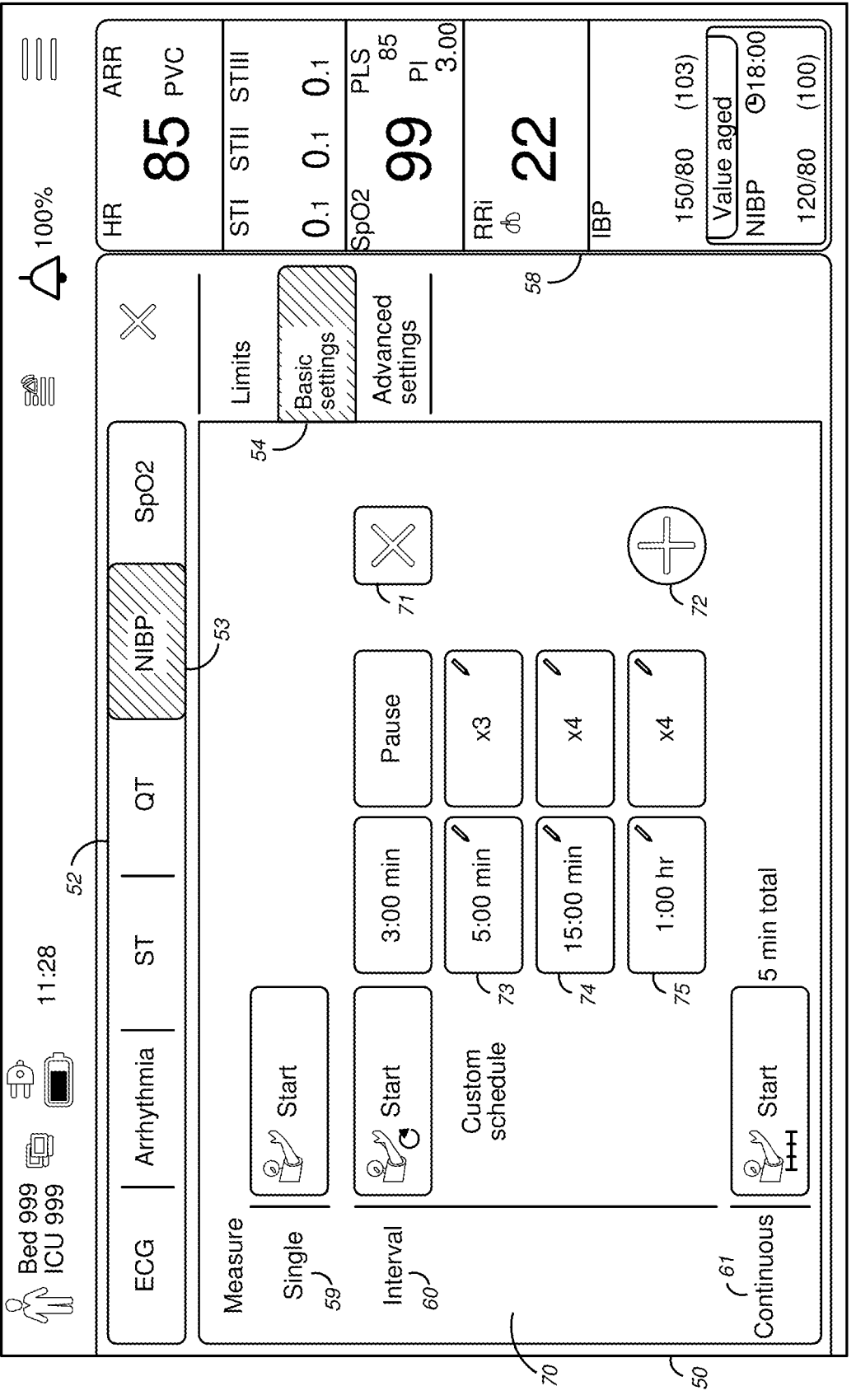

As shown in FIG. 8, while in the custom schedule 70, the user has used selection 72 (e.g., "+") to add yet another measurement schedule 75 (e.g., another cycle of repeated NIBP measurements for four times (e.g., ×4) with 1-hour interval between each measurement) to the custom schedule 70.

Figure 9:
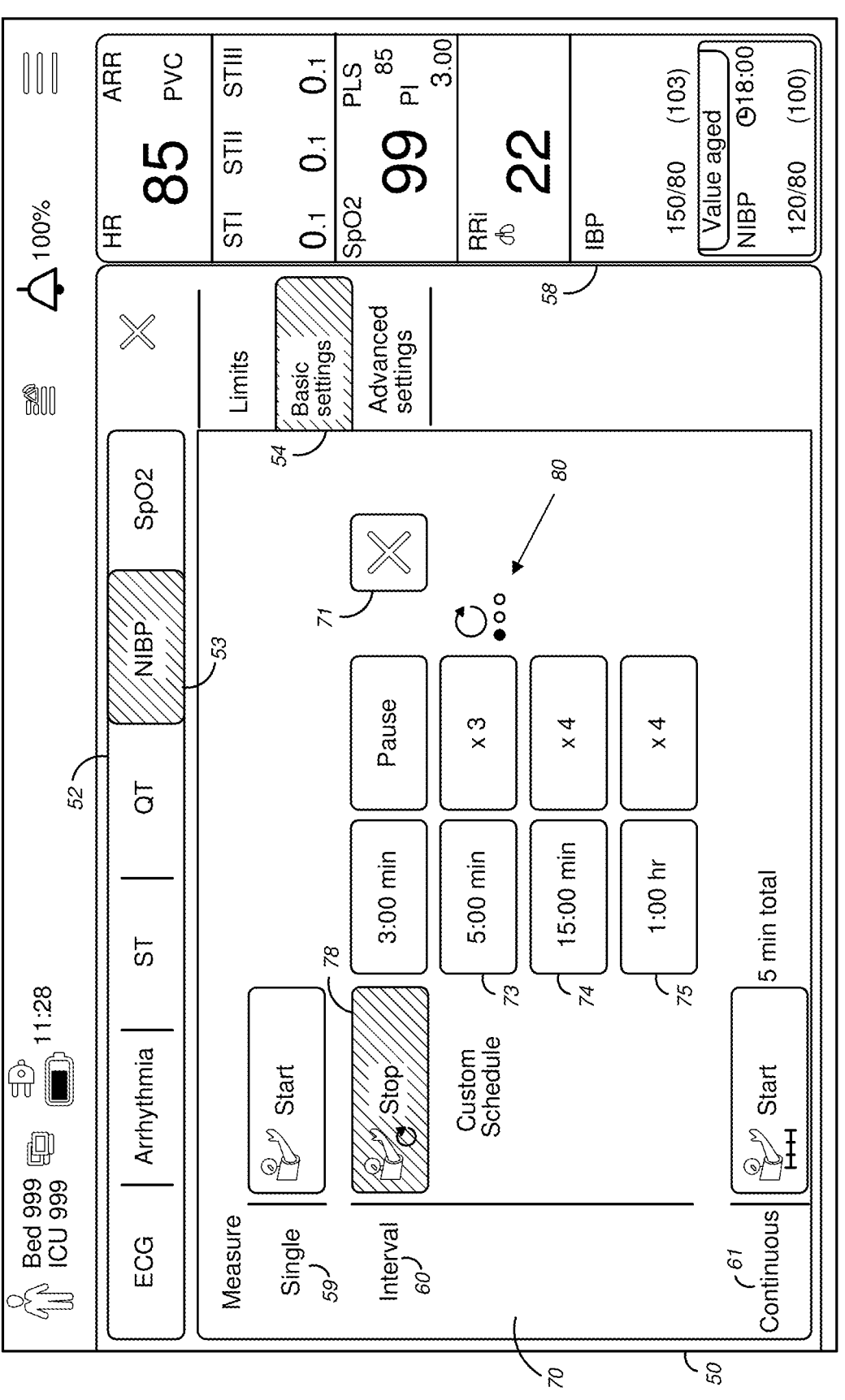

Once the custom schedule 70 is complete, the custom schedule can be executed by the user from the GUI 50, as shown in FIG. 9. As shown in FIG. 9, the user selects "start" 78 from the GUI 50 (e.g., shown as "stop" 78 once selected) to execute the custom schedule 70. Using the custom schedule, one or more cycles of repeated NIBP measurements 73 taken three times (e.g., ×3) with a 5-minute interval between each measurement, followed by NIBP measurements 74 taken four times (e.g., ×4) with a 15-minute interval between each measurement, and then followed by another cycle of repeated NIBP measurements 75 taken four times (e.g., ×4) with 1-hour interval between each measurement are sequentially performed for measuring physiological parameters of the patent 1. The execution of the custom schedule 70 can be indicated by a visual indication 80 provided to the user within the custom schedule 70. Additionally, the visual indication 80 can also be located next to a specific measure schedule (e.g., measure schedule 73) in order to indicate which measurement within a certain cycle is currently in progress. A user can stop the execution of the custom schedule 70 any time by selecting "stop" 78 from the custom schedule 70. As shown in FIG. 9, once "start" 78 is selected the selection changes to "stop" 78. That is, the same selection 78 can be used for both starting and stopping the custom schedule 70.

Figure 10:
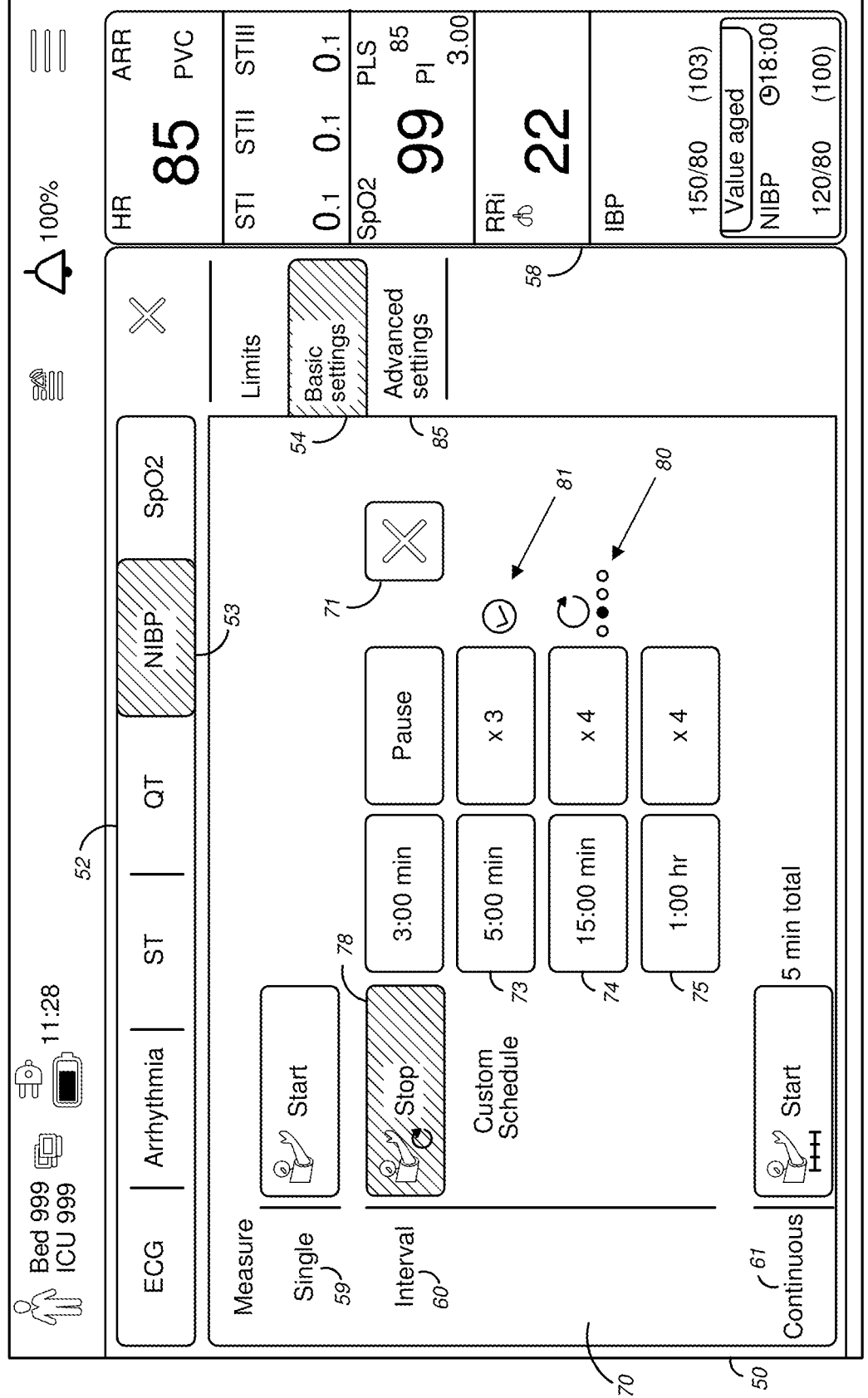

FIG. 10 illustrates an example of the progression of the execution of the custom schedule 70. As shown in FIG. 10, the completion of measurements of the physiological parameters of the patient 1 for each cycle of the custom schedule 70 is indicated by a visual indication or notification 81 (e.g., "check mark") next to the completed measurement 73. In this case, the NIBP measurements 73 to be taken three times (e.g., ×3) with a 5-minute interval between each measurement have been completed for the patient 1. Additionally, another visual indication or notification 80 is provided to indicate that a certain measurement cycle is currently in progress in order to provide real-time the progress of the scheduled measurements of the custom schedule 70. In this case, the NIBP measurements 74 to be taken four times (e.g., ×4) with a 15-minute interval between each measurement is currently in progress. As noted above, the user can stop the execution of the custom schedule 70 any time by selecting "stop" 78.

The GUI 50 can also provide advanced settings 85 that allow the user to configure display settings, adjust interval timing, or other similar settings of the GUI 50. For example, the user can determine the interval time to be aligned with clock or based on actual start time. Further, the display region in the GUI 50 for displaying numerical values of NIBP can also include a notified age of the numerical value.

The GUI 50 described with reference to FIGS. 5-10 provides a user with both predefined intervals for taking physiological measurements of a patient as well as allows the user to change or customize the intervals for taking physiological measurements of a patient, as needed. The GUI 50 allows the user to create a custom schedule with one or more cycles of repeated physiological measurements, and the user is also allowed to adjust the numbers of the measurements and intervals.

Optionally, the user is allowed to add or delete cycles of measurements. With the progress and/or completion of each cycle, the GUI 50 will provide notifications to indicate which measurement within a certain cycle is currently in progress and the completion of each cycle of measurements in order to notify the user in real-time the progress of the scheduled measurements of the patient.

The GUI 50 described with reference to FIGS. 5-10 provides a user with more flexibility in configuring or customizing a physiological measurement schedule for patients to fulfill different clinical needs.

Figure 11:
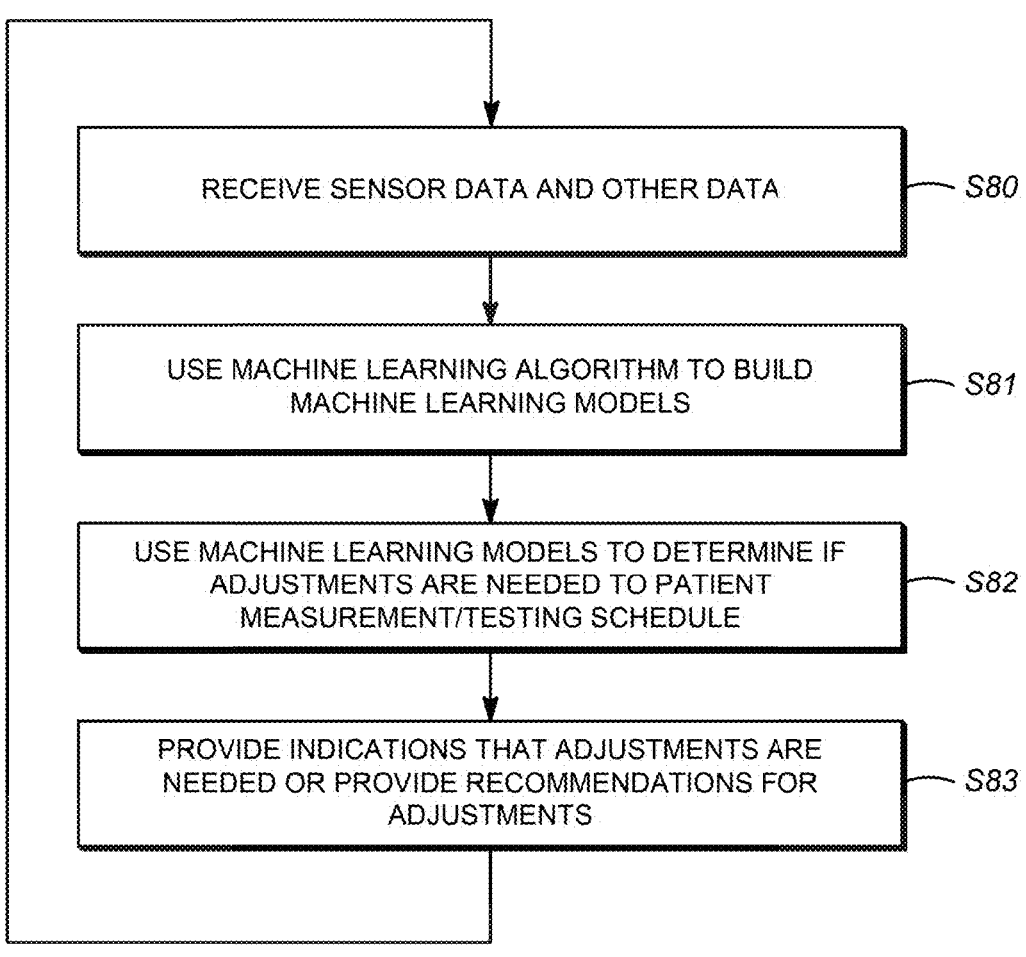
FIG. 11 illustrates an example of a method and an algorithm for automatically adjusting a customizable physiological measurement schedule for measuring physiological parameters according to an embodiment of the present disclosure.

FIG. 11 illustrates an exemplary method and algorithm for automatically adjusting a customizable physiological measurement schedule for measuring physiological parameters according to an embodiment of the present disclosure.

It is contemplated by the present disclosure that the algorithm for automatically adjusting a customizable physiological measurement schedule of the GUI 50 is a machine learning algorithm that includes, but is not limited to, one or more support vector machine learning algorithms, decision tree classifiers, linear discriminant analysis learning algorithms, and artificial neural network learning algorithms. Decision tree classifiers include, but are not limited to, random forest algorithms.

The algorithm for automatically adjusting a customizable physiological measurement schedule of the GUI 50 can be stored in the memory 8, 13, 41, 42 and executed by one or more processors 3, 12, 45 of an electronic device such as, but not limited to, the physiological monitoring device 7, monitor mount 10, or the server/central computer 30, as described with reference to FIGS. 1, 2 and 4.

Referring collectively to FIG. 1 and FIG. 11, in step S80, the electronic device (e.g., the physiological monitoring device 7, monitor mount 10, or the server/central computer 30) containing the machine learning algorithm receives the physiological data collected by the sensors 17 connected the patient 1 (e.g., related to, for example, an ECG, SpO2, NIBP, temperature, and/or etCO2). The electronic device (e.g., the physiological monitoring device 7, monitor mount 10, or the server/central computer 30) containing the machine learning algorithm also receives (e.g., via network access or via access to historical data storage) other patient data such as history of patient physiological data (e.g., data trend) corresponding to the clinical status of the patient, patient's medical record, patient location information and estimate transport and arrival times. The patient location information can be provided, for example, using location data system 26 or location technology can be used along with a hospital layout or a hospital map to track the location of a patient.

In step S81, the machine learning algorithm uses the physiological data and location data of the patient to build and/or train the machine learning algorithm (e.g., build machine learning models). In step S82, the trained machine learning algorithm can be used to determine if adjustments are to be made to the custom schedule 70.

In step S83, the machine learning logic can transmit an indication to the user via the GUI 50 that adjustments to the custom schedule 70 are (e.g., a visual indication or text message). Alternatively, the machine learning logic can learn the patient's vital sign status from the physiological data and patient location information, and provide recommended settings adjustment to the custom schedule 70 of the GUI 50 to satisfy patient needs without requiring a user or care giver to manually create a new custom schedule based on the patient's clinical status and/or change in the patient location (e.g., from transport to operation room).

The method and algorithm described in FIG. 11 automatically provides a user with an indication when adjustments are to be made to a physiological measurement schedule for a patient, which reduces stress and cognitive load on clinicians, supports rapid patient assessment and accurate clinical documentation, and improves overall patient care.

The present disclosure may be implemented as any combination of an apparatus, a system, an integrated circuit, and a computer program on a non-transitory computer readable recording medium. The one or more processors may be implemented as an integrated circuit ("IC"), an application specific integrated circuit ("ASIC"), or large scale integrated circuit ("LSI"), system LSI, super LSI, or ultra LSI components which perform a part, or all of the functions described in the present disclosure. The one or more processors, for example, processor(s) 3 and processor(s) 12 in FIG. 1, microcontrollers 3a and 3b in FIG. 2 and processor (s) in FIG. 4 can be, but are not limited to, a central processing unit ("CPU"), a hardware microprocessor, a multi-core processor, a single core processor, a field programmable gate array ("FPGA"), a microcontroller, an application specific integrated circuit ("ASIC"), a digital signal processor ("DSP"), or other similar processing device capable of executing any type of instructions, algorithms, or software for controlling the operation, and performing the functions of e.g., the physiological monitoring device 7 (as illustrated in FIGS. 1 and 2) and the monitor mount 10 (as illustrated in FIG. 1) and the server/central computer 30 (as illustrated in FIG. 4).

The present disclosure includes the use of computer programs or algorithms. The programs or algorithms can be stored on a non-transitory computer-readable medium for causing a computer, such as the one or more processors, to execute the functions and steps as described with reference to FIGS. 5-11. For example, memory 8 and 13 in FIG. 1, memory 8 in FIG. 2 and main memory 41 in FIG. 4 can be a single memory or one or more memories or memory locations that include, but are not limited to, a random access memory ("RAM"), a memory buffer, a hard drive, a database, an erasable programmable read only memory ("EPROM"), an electrically erasable programmable read only memory ("EEPROM"), a read only memory ("ROM"), a flash memory, hard disk or any other various layers of memory hierarchy. For example, the one or more memories stores software or algorithms with executable instructions and the one or more processors can execute a set of instructions of the software or algorithms in association with generating, displaying, customizing, and executing measurement schedules on a GUI for measuring physiological parameters of patients, as described with reference to FIGS. 5-11.

The computer programs, which can also be referred to as programs, software, software applications, applications, components, or code, include machine instructions for a programmable processor, and can be implemented in a high-level procedural language, an object-oriented programming language, a functional programming language, a logical programming language, or an assembly language or machine language. The term computer-readable recording medium refers to any computer program product, apparatus or device, such as a magnetic disk, optical disk, solid-state storage device, memory, and programmable logic devices ("PLDs"), used to provide machine instructions or data to a programmable data processor, including a computer-readable recording medium that receives machine instructions as a computer-readable signal.

By way of example, a computer-readable medium can comprise DRAM, RAM, ROM, EEPROM, CD-ROM or other optical disk storage, magnetic disk storage or other magnetic storage devices, or any other medium that can be used to carry or store desired computer-readable program code in the form of instructions or data structures and that can be accessed by a general-purpose or special-purpose computer, or a general-purpose or special-purpose processor. Disk or disc, as used herein, include compact disc ("CD"), laser disc, optical disc, digital versatile disc ("DVD"), floppy disk and Blu-ray disc where disks usually reproduce data magnetically, while discs reproduce data optically with lasers. Combinations of the above are also included within the scope of computer-readable media.

Use of the phrases "capable of," "capable to," "operable to," or "configured to" in one or more embodiments, refers to some apparatus, logic, hardware, and/or element designed in such a way to enable use of the apparatus, logic, hardware, and/or element in a specified manner. The subject matter of the present disclosure is provided as examples of apparatus, systems, methods, and programs for performing the features described in the present disclosure. However, further features or variations are contemplated in addition to the features described above. It is contemplated that the implementation of the components and functions of the present disclosure can be done with any newly arising technology that may replace any of the above implemented technologies.

Although specific visual indications are described with reference to FIGS. 5-10 (e.g., check mark, etc.), it is contemplated by the present disclosure that almost any visual indication can be implemented that effectively conveys the status of any measurement schedule and other aspects of the GUI 50 to the user. Additionally, the above description of "selection" or "selections" as described with reference to FIGS. 5-10 (e.g., "start", "stop", etc.) are examples of virtual tab, buttons, icons, labels, or other selectable symbols within the GUI 50 that allow interaction between the user and the GUI 50.

Although FIGS. 7-10 illustrate one selection 72 (e.g., "+") for adding one or more measurement schedules and one selection 71 (e.g., "×") for removing one or more measurement schedules, it is contemplated by the present disclosure that any number of selections can be included in the GUI 50 for adding or removing measurement schedules as well as adding or removing specific features of the measurement schedules.

Additionally, the above description provides examples, and is not limiting of the scope, applicability, or configuration set forth in the claims. Changes may be made in the function and arrangement of elements discussed without departing from the spirit and scope of the disclosure. Various embodiments may omit, substitute, or add various procedures or components as appropriate. For instance, features described with respect to certain embodiments may be combined in other embodiments.

Various modifications to the disclosure will be readily apparent to those skilled in the art, and the generic principles defined herein may be applied to other variations without departing from the spirit or scope of the present disclosure. Throughout the present disclosure the terms "example," "examples," or "exemplary" indicate examples or instances and do not imply or require any preference for the noted examples. Thus, the present disclosure is not to be limited to the examples and designs described herein but is to be accorded the widest scope consistent with the principles and novel features disclosed.

We claim:

1. An electronic device capable of automatically executing and adjusting a customizable physiological measurement schedule for measuring one or more physiological parameters of a patient comprising:

a display configured to display information related to the patient;

a memory configured to store one or more programs;

a sensor interface including amplifying, filtering and analog-to-digital circuitry to receive the one or more physiological parameters from one or more physiological sensors connected to the patient; and one or more processors configured to automatically execute the one or more programs to:

provide a graphical user interface (GUI) on the display for displaying the one or more physiological parameters concurrent with a customizable measurement schedule for the patient with one or more selections of one or more number of measurements, one or more intervals between measurements and one or more duration of measurements, for a plurality of different cycles of measurements, receive an input corresponding to the one or more intervals to adjust the customizable measurement schedule concurrent with displaying the one or more physiological parameters wherein the input is directed to specifying one or more of the number of measurements, the intervals between measurements and the durations of measurements for the plurality of different cycles, wherein the plurality of different cycles differ in one or more of the number of measurements and the interval between measurements, and configure the measurement of the one or more physiological parameters based on the customized measurement schedule by causing the sensor interface to automatically control the one or more physiological sensors to receive one or more updates to the physiological parameters according to the plurality of different cycles of the adjusted customized measurement schedule.

2. The electronic device of claim 1, wherein the one or more processors are further configured to execute the one or more programs to subtract one or more selections of one or more number of measurements, one or more intervals between measurements, one or more duration of measurements and one or more of the different cycles of measurements from the adjusted customized measurement schedule.

3. The electronic device of claim 1, wherein execution of the customizable measurement schedule is related to discrete measurements of any one of non-invasive blood pressure ("NIBP"), temperature, heart rate, an electrocardiogram ("ECG"), non-invasive peripheral oxygen saturation ($SpO2$), end tidal carbon dioxide ($etCO2$), apnea of the patient, neuromuscular transmission ("NMT"), cardiac output ("CO"), and glucose concentration.

4. The electronic device of claim 1, wherein the one or more processors is further configured to suggest numbers of measurements and intervals between measurements based on previously measured one or more physiological parameters.

5. The electronic device of claim 1, wherein the electronic device is a patient monitor.

6. The electronic device of claim 1, wherein the input is entered by a user.

7. The electronic device of claim 1, wherein the plurality of different cycles of measurements comprise:

a first cycle of measurements comprising a first number of measurements and a first interval between the measurements; and a second cycle of measurements comprising a second number of measurements and a second interval between the measurements, wherein at least one of the first number of measurements differs from the second measurement or the first interval between measurements differs from the second interval between measurements.

8. The electronic device of claim 1, wherein the one or more selections further includes a plurality of pre-defined measurement schedules based on clinical needs.

9. The electronic device of claim 8, wherein the one or more processors are further configured to automatically execute the one or more programs to:

receive data comprising patient location information;

automatically select one of the plurality of pre-defined measurement schedules based on the patient location information;

receive the one or more physiological parameters based on the selected pre-defined measurement schedules; and provide the GUI on the display further including displaying the one or more physiological parameters based on the customized measurement schedule concurrent with displaying the customized measurement schedule and a first visible indication as each measurement time and corresponding measurement interval of the customized measurement schedule is completed, wherein the customized measurement schedule is initially based on the selected pre-defined measurement schedule.

10. The electronic device of claim 9, wherein the one or more processors are further configured to execute the one or more programs to provide a second visible indication indicating a current execution of the customizable measurement schedule concurrent with displaying the one or more physiological parameters and the customizable measurement schedule.

11. The electronic device of claim 1, wherein the one or more processors are further configured to automatically execute the one or more programs to:

receive the one or more physiological parameters based on the customized measurement schedule; and provide the GUI on the display further including displaying the one or more physiological parameters based on the customized measurement schedule concurrently with displaying the customized measurement schedule and a first visible indication proximate a given one of the plurality of cycles of measurements currently in progress.

12. The electronic device of claim 1, wherein the one or more processors are further configured to automatically execute the one or more programs to:

receive data comprising patient location information, patient medical condition, and historical physiological parameters of the patient, the historical physiological parameters indicating data trends therein;

execute a machine learning algorithm that automatically determines adjustments to the customized measurement schedule based on the one or more physiological parameters collected by the sensors connected to the patient, the patient location information, and the historical physiological parameters; and provide the GUI on the display further including an indication of the automatically determined adjustments to the customizable measurement schedule based on the historical physiological parameters and the location information.

13. A method of automatically executing and adjusting a customizable physiological measurement schedule for measuring one or more physiological parameters of a patient on an electronic device comprising:

providing a graphical user interface ("GUI") for displaying the one or more physiological parameters concurrently with a customizable measurement schedule for the patient with one or more selections of one or more number of measurements, one or more intervals between measurements and one or more duration of measurements, for a plurality of different cycles of measurements;

receiving an input to the customizable measurement schedule concurrent with displaying the one or more physiological parameters, wherein the input is directed to specifying one or more of the number of measurements, the intervals between measurements and the durations of measurements for the plurality of different cycles, wherein the plurality of different cycles differ in one or more of the number of measurements and the interval between measurements; and configuring measurement of the one or more physiological parameters from physiological data based on the customized measurement schedule by causing a sensor interface to automatically control the one or more physiological sensors to receive one or more updates to the physiological parameters according to the plurality of different cycles of the adjusted customized measurement schedule.

14. The method according to claim 13, further comprising subtracting one or more selections of one or more number of measurements, one or more intervals between measurements, one or more duration of measurements and one or more of the different cycles of measurements from the adjusted customized measurement schedule.

15. The method according to claim 13, wherein the customizable measurement schedule is related to discrete or continuous measurements of any one of non-invasive blood pressure ("NIBP"), temperature, heart rate, an electrocardiogram ("ECG"), non-invasive peripheral oxygen saturation (SpO2), end tidal carbon dioxide (etCO2), apnea of the patient, neuromuscular transmission ("NMT"), cardiac output ("CO"), and glucose concentration.

16. The method according to claim 13, further comprising providing a second visible indication indicating a current execution of the customizable measurement schedule concurrent with displaying the one or more physiological parameters and the customizable measurement schedule.

17. The method according to claim 13, further comprising suggesting numbers of measurements and intervals between measurements based on previously measured one or more physiological parameters.

18. The method according to claim 13, wherein the input is entered by a user.

19. The method according to claim 13, further comprising providing the GUI for further displaying the one or more physiological parameters based on the customized measurement schedule concurrently with displaying the customized measurement schedule and a first visible indication proximate a given one of the plurality of cycles of measurements currently in progress.

20. A non-transitory computer-readable recording medium storing a program for automatically executing and adjusting a customizable physiological measurement schedule for measuring one or more physiological parameters of a patient on an electronic device, the program, when executed by a processor, causes the processor to automatically:

provide a graphical user interface (GUI) on a display for displaying the one or more physiological parameters concurrent with a customizable measurement schedule for the patient with one or more selections of one or more number of measurements, one or more intervals between measurements and one or more duration of measurements, for a plurality of different cycles of measurements;

receive an input to the customizable measurement schedule concurrent with displaying the one or more physiological parameters, wherein the input is directed to specifying one or more of the number of measurements, the intervals between measurements and the durations of measurements for the plurality of different cycles, wherein the plurality of different cycles differ in one or more of the number of measurements and the interval between measurements; and configure measurement of the one or more physiological parameters from the physiological data based on the customized measurement schedule by the one or more processors causing a sensor interface to automatically control the one or more physiological sensors to receive one or more updates to the physiological parameters according to the plurality of different cycles of the adjusted customized measurement schedule.

21. The non-transitory computer-readable recording medium according to claim 20, wherein the processor subtracts one or more selections of one or more number of measurements, one or more intervals between measurements, one or more duration of measurements and one or more of the different cycles of measurements from the adjusted customized measurement schedule.

22. The non-transitory computer-readable recording medium according to claim 20, wherein the customizable measurement schedule is related to discrete or continuous measurements of any one of non-invasive blood pressure (NIBP), temperature, heart rate, electrocardiogram (ECG), non-invasive peripheral oxygen saturation (SpO2), end tidal carbon dioxide (etCO2), apnea of the patient, neuromuscular transmission (NMT), cardiac output (CO), and glucose measurement.

23. The non-transitory computer-readable recording medium according to claim 20, wherein the processor further provides a second visible indication indicating a current execution of the customizable measurement schedule concurrent with displaying the one or more physiological parameters and the customizable measurement schedule.

24. The non-transitory computer-readable recording medium according to claim 20, wherein the program when executed by the processor is further configured to suggest number of measurements and intervals between measurements based on previously measured one or more physiological parameters.

25. The non-transitory computer-readable recording medium according to claim 20, wherein the plurality of different cycles of measurements comprise:

a first cycle of measurements comprising a first number of measurements and a first interval between the measurements; and a second cycle of measurements comprising a second number of measurements and a second interval between the measurements, wherein at least one of the first number of measurements differs from the second measurement or the first interval between measurements differs from the second interval between measurements.

26. The non-transitory computer-readable recording medium according to claim 20, wherein the one or more selections further includes a plurality of pre-defined measurement schedules based on clinical needs.

27. The non-transitory computer-readable recording medium according to claim 26, wherein the one or more processors are further configured to automatically execute the one or more programs to:

receive data comprising patient location information;

automatically select one of the plurality of pre-defined measurement schedules based on the patient location information;

receive the one or more physiological parameters based on the selected pre-defined measurement schedules; and provide the GUI on the display further including displaying the one or more physiological parameters based on the selected pre-defined measurement schedule concurrent with displaying the selected pre-defined measurement schedule and a first visible indication as each measurement time and corresponding measurement interval of the pre-defined measurement schedule is completed.

28. The electronic device of claim 27, further comprising:

a communication interface for receiving the patient location information.

29. The non-transitory computer-readable recording medium according to claim 20, wherein the one or more processors are further configured to automatically execute the one or more programs to:

receive the one or more physiological parameters based on the customized measurement schedule; and provide the GUI on the display further including displaying the one or more physiological parameters based on the customized measurement schedule concurrently with displaying the customized measurement schedule and a first visible indication proximate a given one of the plurality of cycles of measurements currently in progress.

* * * * *